United States Patent
Joseph (10) Patent No.: US 9,039,731 B2
(45) Date of Patent: May 26, 2015

(54) SURGICAL FORCEPS INCLUDING BLADE SAFETY MECHANISM

(75) Inventor: Daniel A. Joseph, Golden, CO (US)

(73) Assignee: Covidien LP, Mansfield, MA (US)

( * ) Notice: Subject to any disclaimer, the term of this patent is extended or adjusted under 35 U.S.C. 154(b) by 474 days.

(21) Appl. No.: 13/466,282

(22) Filed: May 8, 2012

(65) Prior Publication Data

US 2013/0304114 A1    Nov. 14, 2013

(51) Int. Cl.
| A61B 17/00 | (2006.01) |
| A61B 17/285 | (2006.01) |
| A61B 18/14 | (2006.01) |
| A61B 17/28 | (2006.01) |
| A61B 19/00 | (2006.01) |
| A61B 18/00 | (2006.01) |

(52) U.S. Cl.
CPC ....... *A61B 17/285* (2013.01); *A61B 2017/2837* (2013.01); *A61B 2019/481* (2013.01); *A61B 18/1442* (2013.01); *A61B 2018/0063* (2013.01); *A61B 2018/1455* (2013.01); *A61B 2019/4805* (2013.01)

(58) Field of Classification Search
CPC ............. A61B 2018/1455; A61B 2018/00601; A61B 18/1445; A61B 17/32; A61B 2017/2946; A61B 18/085; A61B 18/1442
USPC .................. 606/45, 167, 170, 174, 205–208; 227/175.1–182.1
See application file for complete search history.

(56) References Cited

U.S. PATENT DOCUMENTS

| H1745 H | 8/1998 | Paraschac |
| 5,843,100 A * | 12/1998 | Meade ......................... 606/147 |
| H1904 H | 10/2000 | Yates et al. |
| H2037 H | 7/2002 | Yates et al. |
| D533,274 S | 12/2006 | Visconti et al. |

(Continued)

FOREIGN PATENT DOCUMENTS

| CN | 21299462 | 9/2009 |
| DE | 2415263 A1 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Katherine M Shi (57) ABSTRACT

A forceps includes first and second jaw members and at least one handle movable between an open position and a closed position for moving the jaw members between a spaced-apart position and an approximated position. A ratchet mechanism includes first and second ratchet components configured to engage one another upon movement of the at least one handle to the closed position to retain the jaw members in the approximated position. A knife is selectively movable between a retracted position and an extended position, wherein the knife extends between the jaw members to cut tissue therebetween. A safety mechanism is configured to inhibit extension of the knife when the jaw members are disposed in the spaced-apart position. Movement of the ratchet components into engagement with one another to retain the jaw members in the approximated position disengages the safety mechanism, thereby permitting extension of the knife.

13 Claims, 5 Drawing Sheets

(56) References Cited

U.S. PATENT DOCUMENTS

| | | |
|---|---|---|
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,789,878 B2 | 9/2010 | Dumbauld et al. |
| 7,811,283 B2 | 10/2010 | Moses et al. |
| D627,462 S | 11/2010 | Kingsley |
| D628,289 S | 11/2010 | Romero |
| D628,290 S | 11/2010 | Romero |
| 7,857,812 B2 | 12/2010 | Dycus et al. |
| D630,324 S | 1/2011 | Reschke |
| 7,922,718 B2 | 4/2011 | Moses et al. |
| 7,942,303 B2 | 5/2011 | Shah |
| D649,249 S | 11/2011 | Guerra |
| D649,643 S | 11/2011 | Allen, IV et al. |
| D661,394 S | 6/2012 | Romero et al. |
| 8,333,765 B2 | 12/2012 | Johnson et al. |
| 8,454,602 B2 | 6/2013 | Kerr et al. |
| 8,523,898 B2 | 9/2013 | Bucciaglia et al. |
| 8,529,566 B2 | 9/2013 | Kappus et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,679,140 B2 | 3/2014 | Butcher |
| 8,685,009 B2 | 4/2014 | Chernov et al. |
| 8,685,056 B2 | 4/2014 | Evans et al. |
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,900,232 B2 | 12/2014 | Ourada |
| 8,939,972 B2 | 1/2015 | Twomey |
| 8,961,513 B2 | 2/2015 | Allen, IV et al. |
| 8,961,514 B2 | 2/2015 | Garrison |
| 8,961,515 B2 | 2/2015 | Twomey et al. |
| 8,968,283 B2 | 3/2015 | Kharin |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 2006/0167452 A1 | 7/2006 | Moses et al. |
| 2007/0088356 A1* | 4/2007 | Moses et al. ............ 606/51 |
| 2008/0033428 A1 | 2/2008 | Artale et al. |
| 2011/0054469 A1 | 3/2011 | Kappus et al. |
| 2012/0059409 A1* | 3/2012 | Reschke et al. ............ 606/208 |
| 2012/0083786 A1 | 4/2012 | Artale et al. |
| 2012/0239034 A1 | 9/2012 | Horner et al. |
| 2012/0259331 A1 | 10/2012 | Garrison |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296371 A1 | 11/2012 | Kappus et al. |
| 2012/0303025 A1 | 11/2012 | Garrison |
| 2012/0303026 A1 | 11/2012 | Dycus et al. |
| 2012/0310240 A1 | 12/2012 | Olson et al. |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1 | 1/2013 | Sims et al. |
| 2013/0022495 A1 | 1/2013 | Allen, IV et al. |
| 2013/0046295 A1 | 2/2013 | Kerr et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0138101 A1 | 5/2013 | Kerr |
| 2013/0138129 A1 | 5/2013 | Garrison et al. |
| 2013/0144284 A1 | 6/2013 | Behnke, II et al. |
| 2013/0178852 A1 | 7/2013 | Allen, IV et al. |
| 2013/0185922 A1 | 7/2013 | Twomey et al. |
| 2013/0197503 A1 | 8/2013 | Orszulak |
| 2013/0226178 A1 | 8/2013 | Brandt et al. |
| 2013/0245623 A1 | 9/2013 | Twomey |
| 2013/0253489 A1 | 9/2013 | Nau, Jr. et al. |
| 2013/0255063 A1 | 10/2013 | Hart et al. |
| 2013/0274736 A1 | 10/2013 | Garrison |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0325057 A1 | 12/2013 | Larson et al. |
| 2014/0005663 A1 | 1/2014 | Heard et al. |
| 2014/0005666 A1 | 1/2014 | Moua et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| JP | 61-501068 | 9/1984 |

(56) References Cited

FOREIGN PATENT DOCUMENTS

| | | |
|---|---|---|
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 9-10223 C | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02045589 A3 | 9/2002 |
| WO | 2005110264 A3 | 4/2006 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. TT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery", Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surge" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.

(56) References Cited

OTHER PUBLICATIONS

Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 006233.8 dated Feb. 2, 2012.
Int'l Search Report EP 11 007972.0 dated Dec. 28, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.

(56) References Cited

OTHER PUBLICATIONS

Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
U.S. Appl. No. 08/926,869, filed Sep. 10, 1997.
U.S. Appl. No. 09/177,950, filed Oct. 23, 1998.
U.S. Appl. No. 09/387,883, filed Sep. 1, 1999.
U.S. Appl. No. 09/591,328, filed Jun. 9, 2000.
U.S. Appl. No. 12/336,970, filed Dec. 17, 2008.

\* cited by examiner

SURGICAL FORCEPS INCLUDING BLADE SAFETY MECHANISM

BACKGROUND

1. Technical Field

The present disclosure relates to surgical instruments and, more particularly, to an open surgical forceps for grasping, treating, and/or cutting tissue.

2. Background of Related Art

A forceps is a plier-like instrument which relies on mechanical action between its jaw members to grasp, clamp, and constrict tissue. Electrosurgical forceps utilize both mechanical clamping action and electrical energy to effect hemostasis by heating tissue to coagulate, cauterize, or otherwise treat tissue. Certain surgical procedures require more than simply coagulation and/or cauterization and rely on the unique combination of clamping pressure, precise electrosurgical energy control, and gap distance (i.e., the distance between opposing jaw members of the forceps when closed about tissue) to "seal" tissue.

Typically, once tissue has been treated, e.g., sealed, the user has to accurately sever the tissue along the newly formed tissue seal. Accordingly, many forceps have been designed which incorporate a knife or blade member which effectively severs the tissue after forming a tissue seal.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any of the other aspects described herein.

In accordance with aspects of the present disclosure, a forceps is provided including an end effector assembly having first and second jaw members movable relative to one another between a spaced-apart position and an approximated position for grasping tissue therebetween. One or more handles is coupled to the end effector assembly and is movable between an open position and a closed position for moving the jaw members between the spaced-apart position and the approximated position. A ratchet mechanism includes first and second ratchet components configured to engage one another upon movement of the handle(s) to the closed position to retain the jaw members in the approximated position. A knife is selectively movable between a retracted position and an extended position, wherein the knife extends between the jaw members to cut tissue therebetween. A safety mechanism configured to inhibit extension of the knife when the jaw members are disposed in the spaced-apart position is also provided and is configured such that, upon movement of the ratchet components into engagement with one another to retain the jaw members in the approximated position, the safety mechanism is disengaged, thereby permitting extension of the knife.

In one aspect, a trigger assembly is coupled to the knife. The trigger assembly includes a trigger movable between a first position and a second position for moving the knife between the retracted position and the extended position.

In another aspect, the trigger assembly further includes a belt rotatably disposed about first and second posts. The trigger is coupled to the belt on one side thereof and the knife is coupled to the belt on the other side thereof such that movement of the trigger in a first direction effects rotation of the belt about the first and second posts and movement of the knife in a second, opposite direction.

In another aspect, the safety mechanism includes a pivot member pivotable between a first position, wherein a portion of the pivot member is disposed in a travel path of the trigger to inhibit movement of the trigger from the first position, and a second position, wherein the portion of the pivot member is displaced from the travel path of the trigger to permit movement of the trigger from the first position. Further, the pivot member may be biased towards the first position.

In still another aspect, the forceps is configured such that, upon movement of the ratchet components into engagement with one another, one of the ratchet components urges the pivot member to rotate from the first position to the second position, thereby disengaging the safety mechanism.

In yet another aspect, in the second position, the portion of the trigger is positioned adjacent one of the first and second ratchet components to substantially inhibit disengagement of the first and second ratchet components from one another.

In still yet another aspect, the handle(s) is movable from the open position to a plurality of closed positions for moving the jaw members between the spaced-apart position and a plurality of approximated positions, and wherein the ratchet components are configured to engage one another at a plurality of incremental positions corresponding to the plurality of approximated positions of the jaw members.

Provided in accordance with other aspects of the present disclosure is a forceps including an end effector assembly having first and second jaw members movable relative to one another between a spaced-apart position and an approximated position for grasping tissue therebetween. One or more handles is coupled to the end effector assembly and is movable between an open position and a closed position for moving the jaw members between the spaced-apart position and the approximated position. A ratchet mechanism including first and second ratchet components configured to engage one another upon movement of the handle(s) to the closed position to retain the jaw members in the approximated position is also provided. A knife is selectively movable between a retracted position and an extended position, wherein the knife extends between the jaw members to cut tissue therebetween. A trigger is coupled to the knife and is movable between a first position and a second position for moving the knife between the retracted position and the extended position. In the second position, a portion of the trigger is positioned adjacent one of the first and second ratchet components to substantially inhibit disengagement of the first and second ratchet components from one another.

In one aspect, the forceps further includes a belt rotatably disposed about first and second posts. The trigger is coupled to the belt on one side thereof and the knife is coupled to the belt on the other side thereof such that movement of the trigger in a first direction effects rotation of the belt about the first and second posts and movement of the knife in a second, opposite direction.

In another aspect, the handle(s) is movable from the open position to a plurality of closed positions for moving the jaw members between the spaced-apart position and a plurality of approximated positions. The ratchet components are configured to engage one another at a plurality of incremental positions corresponding to the plurality of approximated positions of the jaw members.

In still another aspect, one or both of the ratchet components are formed partially or entirely from a flexible material to permit manual override to disengage the ratchet components from one another when the trigger is disposed in the second position.

In yet another aspect, a safety mechanism is provided to inhibit movement of the trigger to the second position when the jaw members are disposed in the spaced-apart position. Movement of the ratchet components into engagement with one another to retain the jaw members in the approximated position disengages the safety mechanism, thereby permitting movement of the trigger to the second position.

In still yet another aspect, the safety mechanism includes a pivot member pivotable between a first position, wherein a portion of the pivot member is disposed in a travel path of the trigger to inhibit movement of the trigger from the first position, and a second position, wherein the pivot member is displaced from the travel path of the trigger to permit movement of the trigger from the first position.

In another aspect, the forceps is configured such that, upon movement of the ratchet components into engagement with one another, one of the ratchet components urges the pivot member to rotate from the first position to the second position, thereby disengaging the safety mechanism.

A forceps provided in accordance with other aspects of the present disclosure includes first and second jaw members movable relative to one another between a spaced-apart position and an approximated position for grasping tissue therebetween. First and second shaft members are coupled to the first and second jaw members, respectively, and are movable relative to one another between an open position and a closed position for moving the jaw members between the spaced-apart position and the approximated position. A ratchet mechanism including first and second ratchet components disposed on the first and second shaft members, respectively, is also provided. The ratchet components are configured to engage one another upon movement of the shaft members to the closed position to retain the jaw members in the approximated position. A knife assembly disposed within the first shaft member and including a knife selectively movable between a retracted position and an extended position, wherein the knife extends between the jaw members to cut tissue therebetween, is also included. Further, a safety mechanism disposed within the first shaft member is configured to inhibit extension of the knife when the jaw members are disposed in the spaced-apart position. Movement of the ratchet components into engagement with one another to retain the jaw members in the approximated position disengages the safety mechanism, thereby permitting extension of the knife. A trigger disposed on the first shaft member and coupled to the knife is movable between a first position and a second position for moving the knife between the retracted position and the extended position. In the second position, a portion of the trigger is positioned adjacent the second ratchet component to substantially inhibit disengagement of the first and second ratchet components from one another.

In one aspect, the safety mechanism includes a pivot member pivotable between a locked position, wherein a portion of the pivot member is disposed in a travel path of the trigger to inhibit movement of the trigger from the first position, and an unlocked position, wherein the pivot member is displaced from the travel path of the trigger to permit movement of the trigger from the first position.

In another aspect, upon movement of the ratchet components into engagement with one another, the second ratchet component urges the pivot member to rotate from the locked position to the unlocked position, thereby disengaging the safety mechanism.

In yet another aspect, the first and second shaft members are movable from the open position to a plurality of closed positions for moving the jaw members between the spaced-apart position and a plurality of approximated positions. Further, the ratchet components are configured to engage one another at a plurality of incremental positions corresponding to the plurality of approximated positions of the jaw members.

In another aspect, the first ratchet components is formed partially or entirely from a flexible material to permit manual override to disengage the ratchet components from one another when the trigger is disposed in the second position.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
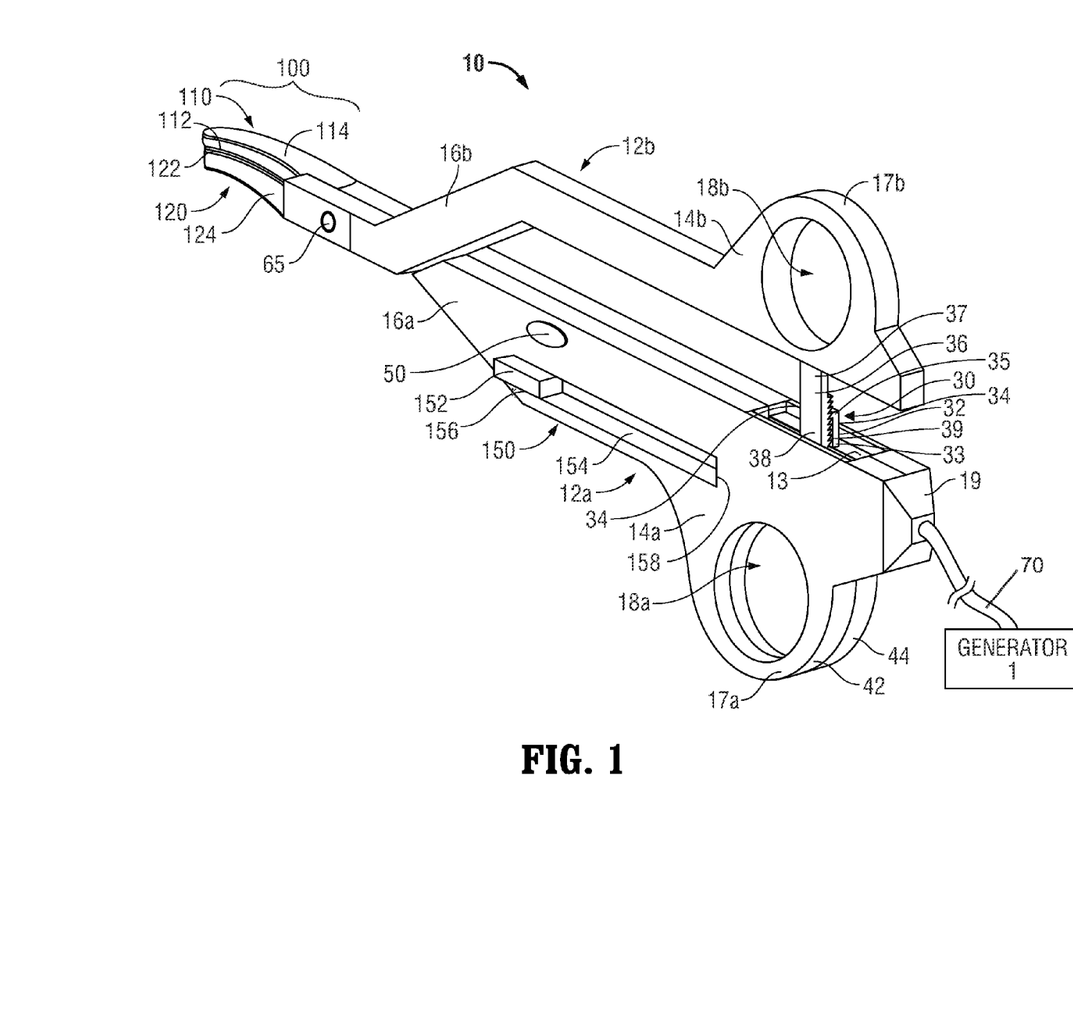
FIG. 1 is a rear, perspective view of an open surgical forceps provided in accordance with the present disclosure.

Referring initially to FIG. 1, an open surgical forceps provided in accordance with the present disclosure is shown generally identified by reference numeral 10. Although described with respect to open surgical forceps 10, the present disclosure is equally applicable for use with endoscopic forceps or any other suitable surgical instruments. Forceps 10 includes a first and second shaft members 12a, 12b, each having a proximal end 14a, 14b and a distal end 16a, 16b, respectively. Forceps 10 further includes an end effector assembly 100 having first and second jaw members 110, 120 that respectively attach to distal ends 16a, 16b of first and second shaft members 12a, 12b. First and second jaw members 110, 120 are pivotably connected about a pivot pin 65 and are movable relative to one another to grasp tissue therebetween, as will be described in greater detail below.

Each of first and second shaft members 12a, 12b includes a handle 17a, 17b disposed at the respective proximal end 16a, 16b thereof. Each handle 17a, 17b defines a finger hole 18a, 18b therethrough for receiving a finger of the user. Finger holes 18a, 18b facilitate movement of first and second shaft members 12a, 12b relative to one another between an open position (FIG. 2), wherein jaw members 110, 120 are disposed in spaced-apart relation relative to one another, and one or more closed position (FIGS. 1, 3, and 4), wherein jaw members 110, 120 are approximated relative to one another to grasp tissue therebetween.

One of the shaft members, e.g., first shaft member 12a, includes a proximal shaft connector 19 that is designed to connect forceps 10 to a source of energy, e.g., electrosurgical generator 1, although forceps 10 may alternatively be configured as a battery-powered instrument. Proximal shaft connector 19 secures a cable 70 to forceps 10 for supplying energy from generator 1 to either (or both) of jaw members 110, 120. More specifically, one or more wires (not explicitly shown)

extend through cable 70 and first shaft member 12a to electrically couple either (or both) of tissue sealing plates 112, 122 of jaw members 110, 120, respectively, to generator 1. One or more of the wires (not explicitly shown) may also couple to activation button 50 disposed on first shaft member 12a to allow the user to selectively apply energy to tissue sealing plates 112, 122 for conducting energy therebetween to treat, e.g., seal, tissue grasped therebetween.

With continued reference to FIG. 1, a ratchet mechanism 30 including first and second selectively engagable ratchet components 32, 36 is also provided for selectively locking jaw members 110, 120 relative to one another at various positions during pivoting. First ratchet component 32 of first shaft member 12a is positioned at proximal end 14a of shaft member 12a and extends therefrom towards second shaft member 12b. First ratchet component 32 is engaged to first shaft member 12a at a fixed end 33 thereof and extends in cantilever fashion therefrom to free end 34 thereof. A ratchet tooth 35 is disposed at free end 34 of the cantilevered first ratchet component 32. First ratchet component 32 is formed at least partially from a flexible material to allow flexion of free end 34 thereof relative to fixed end 33 thereof. Further, first ratchet component 32 is positioned adjacent a slot 13 defined within first shaft member 12a that is configured to receive second ratchet component 26 of second shaft member 12b to facilitate engagement of first and second ratchet components 32, 36, respectively, to one another.

Second ratchet component 36 of second shaft member 12b includes a fixed end 37 that is engaged with second shaft member 12b and extends therefrom towards first shaft member 12a. Second ratchet component 36 include a plurality of ratchet teeth 39 disposed between fixed end 37 and free end 38 thereof that are shaped complementarily to ratchet tooth 35 of first ratchet component 32. Second ratchet component 36 is formed from a substantially rigid material such that fixed and free ends 37, 38, respectively, of second ratchet component 36 are maintained in substantially fixed position relative to one another. Ratchet teeth 39 of second ratchet component 36 are configured such that ratchet tooth 35 of first ratchet component 32 may be incrementally engaged between any adjacent ratchet teeth 39 of second ratchet component 36 to retain first and second shaft members 12a, 12b in one or more fixed positions relative to one another corresponding to one or more approximated positions of jaw members 110, 120. Ratchet mechanism 30 may include graduations or other visual markings disposed on one or both of first and second ratchet components 32, 36 that enable the user to easily and quickly ascertain and control the gap distance and/or amount of closure force between the jaw members 110, 120.

Continuing with reference to FIG. 1, as mentioned above, jaw members 110, 120 of end effector assembly 100 are pivotable about pivot pin 65 between the spaced-apart position (FIG. 2) to one or more approximated positions (FIGS. 1, 3 and 4) for grasping tissue therebetween. Jaw member 110 includes an insulated outer housing 114 that is configured to mechanically engage an electrically conductive tissue sealing plate 112 of jaw member 110. Similarly, jaw member 120 includes an insulated outer housing 124 that is configured to mechanically engage an electrically conductive tissue sealing plate 122 of jaw member 120. Tissue Sealing plates 112, 122 are coupled to generator 1, as mentioned above, and oppose one another such that, upon activation, e.g., upon activation of activation switch 50, energy is supplied to and conducted between tissue sealing plates 112, 122 to treat, e.g., seal, tissue grasped therebetween. One or both tissue sealing plates 112, 122 may further define a knife channel 115a, 115b (FIGS. 2-4) extending longitudinally therethrough. Knife channels 115a, 115b (FIGS. 2-4) are configured to receive a cutting member, e.g., knife 174 (FIGS. 2-4), therethrough to facilitate the cutting of tissue grasped between jaw members 110, 120.

Figure 2:
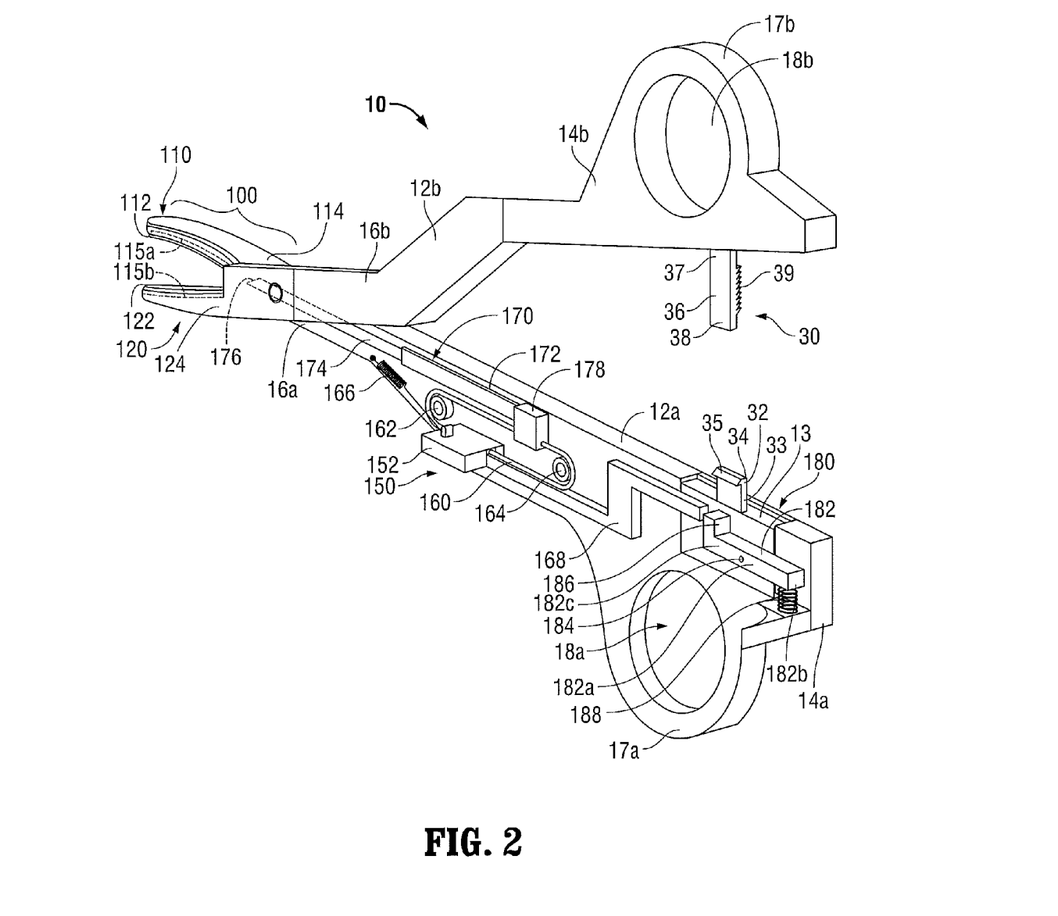
FIG. 2 is a rear, perspective, cut-away view of the forceps of FIG. 1, wherein the jaw members of the forceps are disposed in a spaced-apart position.
Figure 3:
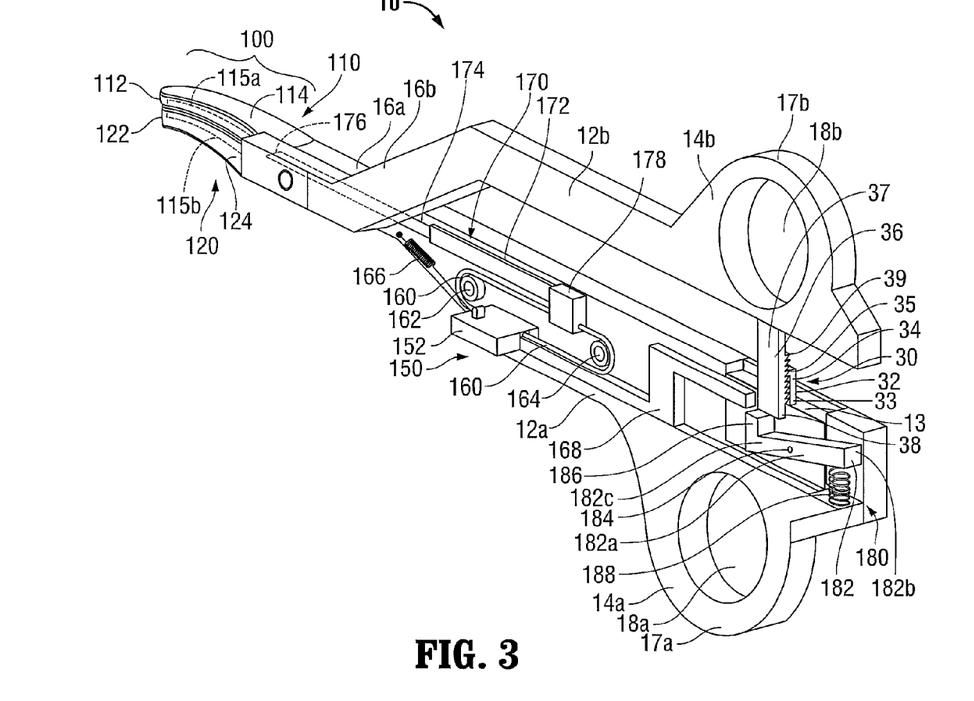
FIG. 3 is a rear, perspective, cut-away view of the forceps of FIG. 1, wherein the jaw members are disposed in an approximated position and the knife is disposed in a retracted position.
Figure 4:
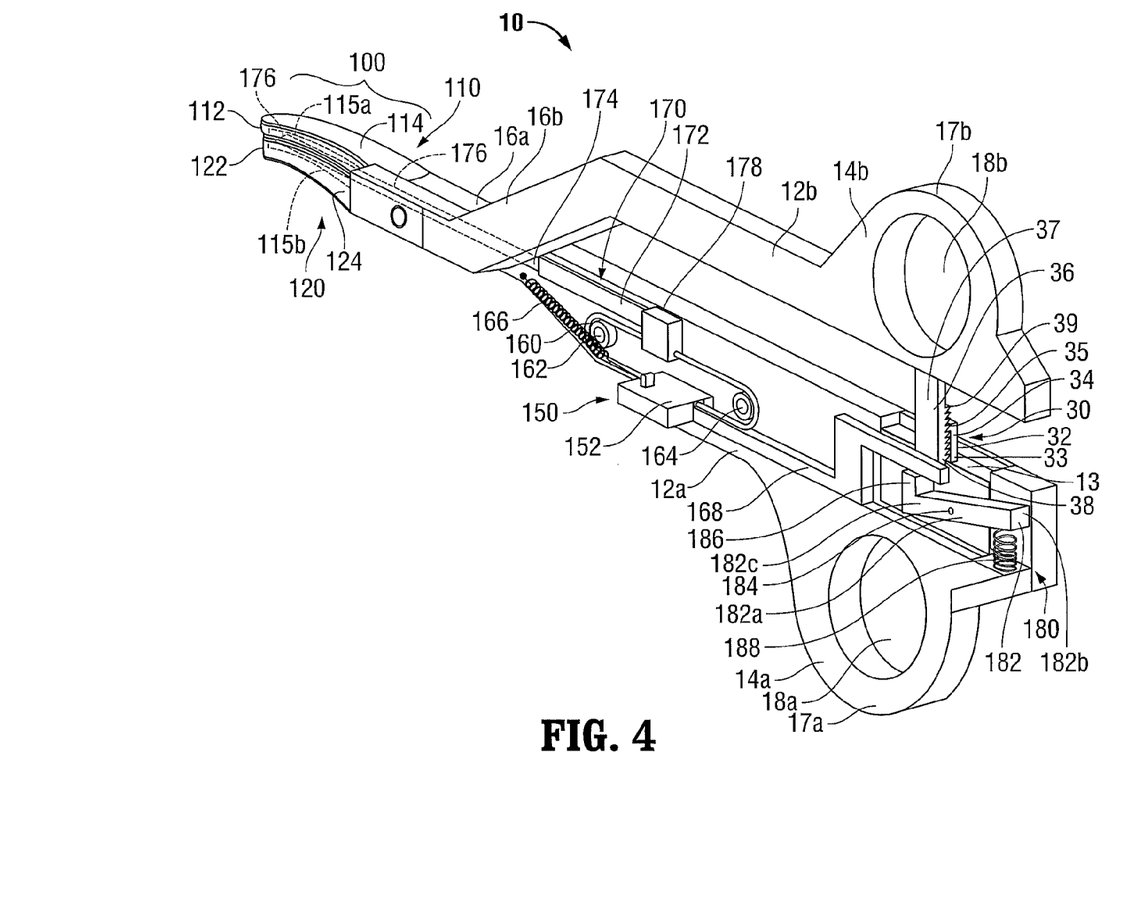
FIG. 4 is a rear, perspective, cut-away view of the forceps of FIG. 1, wherein the jaw members are disposed in the approximated position and the knife is disposed in an extended position.

Turning now to FIGS. 2-4, in conjunction with FIG. 1, one of the shaft members, e.g., first shaft member 12a, is constructed from two half-components 42, 44 that cooperate to form first shaft member 12a and to house the internal working components thereof. More specifically, half-components 42, 44 of first shaft member 12a house a trigger assembly 150, a knife assembly 170, and a safety mechanism 180 which, as will be described in greater detail below, cooperate to permit selective deployment of knife 174 between jaw members 110, 120 and through knife channels 115a, 115b to cut tissue grasped between jaw members 110, 120 only when jaw members 110, 120 are disposed in one of the approximated positions and to inhibit return of jaw members 110, 120 back to the spaced-apart position when knife 174 is deployed therebetween.

Knife assembly 170 generally includes a knife bar 172 engaging a knife 174 at the distal end thereof. Knife 174 defines a distal cutting blade 176 configured to facilitate cutting of tissue upon translation of knife 174 through tissue. The proximal end of knife bar 172 is coupled to knife holder 178, which engages belt 160 of trigger assembly 150 such that, upon actuation of trigger 152 of trigger assembly 150, knife bar 172 is translated distally through first shaft member 12a to translate knife 174 from a retracted position (FIG. 3), wherein knife 174 is disposed proximally of jaw members 110, 120, and an extended position (FIG. 4), wherein knife 174 extends at least partially between jaw members 110, 120, e.g., through knife channels 115a, 115b, respectively, thereof, to cut tissue grasped between jaw members 110, 120.

Trigger assembly 150 generally includes a trigger 152 extending through a slot 154 defined within first shaft member 12a, and a belt 160 rotatably mounted within first shaft member 12a about first and second posts 162, 164, respectively. Trigger 152 extends outwardly from slot 154 of first shaft member 12a to facilitate actuation by the user. That is, trigger 152 is translatable along slot 154 from distal end 156 thereof to proximal end 158 thereof to deploy knife 174 from the retracted position (FIG. 3) to the extended position (FIG. 4). More specifically, trigger 152 is engaged to belt 160 opposite knife holder 178 such that proximal translation of trigger 152 rotates belt 160 about posts 162, 164 to translate knife holder 178 and, thus, knife 174 distally towards the extended position. Distal translation of trigger 152, on the other hand, rotates belt 160 about posts 162, 164 in the opposite direction, thereby translating knife holder 178 and, thus, knife 174 proximally towards the retracted position. Further, trigger 152 is biased towards proximal end 158 of slot 154 via spring 166 such that knife 174 is biased towards the retracted position.

With continued reference to FIGS. 2-4, in conjunction with FIG. 1, trigger 152 further includes a proximal extension 168 extending proximally therefrom within first shaft member 12a. Proximal extension 168 is fixedly engaged to trigger 152 such that translation of trigger 152 along slot 154 effects corresponding movement of proximal extension 168 within first shaft member 12a. As such, when trigger 152 is disposed at distal end 156 of slot 154, proximal extension 168 is disposed in a first position, wherein proximal extension 168 is positioned proximally of ratchet mechanism 30. On the other hand, when trigger 152 is moved to proximal end 158 of slot 154, proximal extension 168 is moved to a second position, wherein proximal extension 168 extends along and adjacent to second ratchet component 36 of second shaft member 12b (which extends through slot 13 of first shaft member 12a to permit engagement of ratchet components 32, 36 to retain jaw members 110, 120 in one of the approximated positions). With proximal extension 168 disposed in the second position wherein proximal extension 168 extends along and adjacent to ratchet component 36 of second shaft member 12b, disengagement of ratchet components 32, 36 of ratchet mechanism 30 is inhibited and, thus, jaw members 110, 120 are retained in the one of the approximated positions.

Safety mechanism 180 is disposed within first shaft member 12a at proximal end 14a thereof and includes a pivot bar 182 pivotably coupled to first shaft member 12a via a pivot pin 184. More specifically, pivot pin 184 extends through an aperture defined within intermediate portion 182a of pivot bar 182, while proximal portion 182b of pivot bar 182 extends proximally from pivot pin 184, and distal portion 182c of pivot bar 182 extends distally from pivot pin 184. Distal portion 182c of pivot bar 182 includes a finger 186 extending therefrom. A spring 188 interconnecting proximal portion 182b of pivot bar 182 and an inner surface of first shaft member 12a biases pivot bar 182 towards a locked position corresponding to a locked condition of safety mechanism 180. In this locked condition, as shown in FIG. 2, finger 186 of distal portion 182c of pivot bar 182 is disposed within the travel path of proximal extension 168 of trigger 152 and abuts the proximal surface of proximal extension 168 of trigger 152, thereby inhibiting actuation of trigger 152 to deploy knife 174. When pivot bar 182 is rotated to an unlocked position, corresponding to the unlocked condition of safety mechanism 180, e.g., under urging of second ratchet component 36 of second shaft member 12b which extends through slot 13 of first shaft member 12a and into contact with distal portion 182c of pivot bar 182 upon movement of jaw members 110, 120 to one of the approximated positions, finger 186 is rotated out of the travel path of proximal extension 168 and, thus, actuation of trigger 152 to deploy knife 174 between jaw members 110, 120 is permitted.

With reference to FIGS. 2-4, in conjunction with FIG. 1, the use and operation of forceps 10 is described. Initially, as shown in FIG. 2, first and second shaft members 12a, 12b are disposed in the open position and, correspondingly, jaw members 110, 120 are disposed in the spaced-apart position. In this position, trigger 152 is disposed at proximal end 156 of slot 154 and, accordingly, knife 174 is disposed in the retracted position. Further, safety mechanism 180 is disposed in the locked condition wherein finger 186 of pivot bar 182 is disposed within the travel path of proximal extension 168 of trigger 152 and abuts the proximal surface of proximal extension 168 of trigger 152, thereby inhibiting actuation of trigger 152 to deploy knife 174. With jaw members 110, 120 disposed in the spaced-apart position, end effector assembly 100 may be maneuvered and/or manipulated into position such that tissue to be grasped, treated, and/or divided is disposed between tissue sealing plates 112, 122 of jaw members 110, 120, respectively.

As shown in FIG. 3, in order to grasp tissue between jaw members 110, 120, first and second shaft members 12a, 12b are moved towards one another, e.g., from the open position towards the one or more closed positions, such that jaw members 110, 120 are approximated about tissue disposed therebetween. Upon further movement of first and second shaft members 12a, 12b towards the closed positions, second ratchet component 36 of second shaft member 12b is inserted at least partially into slot 13 defined within first shaft member 12a and simultaneously or near simultaneously therewith, ratchet tooth 35 of first ratchet component 32 is engaged between any pair of adjacent ratchet teeth 39 of second ratchet component 36 to retain jaw members 110, 120 in one of the approximated positions grasping tissue therebetween.

The gap distance between jaw members 110, 120 and the closure pressure applied to tissue grasped therebetween is determined at least in part by which ratchet teeth 39 ratchet tooth 35 engages. For example, jaw members 110, 120 may be retained in a first approximated position, wherein ratchet tooth 35 is engaged with ratchet teeth 39 disposed adjacent free end 38 of second ratchet component 36, a second approximated position, wherein ratchet tooth 35 is engaged within ratchet teeth 39 disposed adjacent fixed end 37 of second ratchet component 36, or at any incremental position therebetween. As can be appreciated, in the first approximated position, the gap distance between jaw members 110, 120 is relatively smaller and/or the closure pressure applied to tissue grasped therebetween is relatively greater as compared to the second approximated position. Thus, a desired approximated position may be achieved in accordance with a desired gap distance and/or closure pressure, which may ultimately depend on the particular procedure to be performed, the size and/or composition of tissue to be treated, or other factors.

Continuing with reference to FIG. 3, as mentioned above, upon movement of jaw members 110, 120 to one of the approximated positions, second ratchet component 36 of second shaft member 12b is inserted at least partially into slot 13 defined within first shaft member 12a. Upon insertion of second ratchet component 36 into slot 13, free end 38 of second ratchet component 36 contacts distal portion 182c of pivot bar 182 and urges pivot bar 182 to rotate about pivot pin 184 and against the bias of spring 188 to the unlocked position, wherein finger 186 is rotated out of the travel path of proximal extension 168 of trigger 152. That is, upon movement of jaw members 110, 120 to one of the approximated positions, safety mechanism 180 is transitioned to the unlocked condition wherein trigger 152 may be selectively actuated to deploy knife 174 between jaw members 110, 120 to cut tissue grasped therebetween.

With jaw members 110, 120 retained in one of the approximated positions grasping tissue therebetween, energy may be transmitted to one or both of tissue sealing plates 112, 122, e.g., via activation of activation switch 50 (FIG. 1), and conducted through tissue grasped therebetween to treat, e.g., seal, tissue. In procedures where tissue cutting is not desired, at the completion of tissue treatment (or in other instances where it is otherwise desired to release the grasp of tissue between jaw members 110, 120), ratchet mechanism 30 may be disengaged such that first and shaft members 12a, 12b may be returned to the open position, thereby returning jaw members 110, 120 to the spaced-apart position to release tissue. More specifically, in order to disengage ratchet mechanism 30, first and second shaft members 12a, 12b are moved laterally apart from one another slightly but sufficiently so as to disengage tooth 35 from teeth 39, thereby disengaging ratchet mechanism 30. This slight lateral movement of first and second shaft members 12a, 12b is permitted despite the pivotable coupling of first and second shaft members 12a, 12b due to a minimal amount of inherent play in the pivotable coupling and does not disturb the function of forceps 10. Further, slot 12 defined within first shaft member 12a, through which second ratchet component 36 extends, defines a sufficiently great width dimension as compared to the width of second ratchet component 36 to permit lateral movement of second ratchet component 36 therein, thereby allowing for lateral movement of first and second shaft members 12a, 12b relative to one another to disengage ratchet mechanism 30. The lateral movement of first and second shaft members 12a, 12b may be effected via single-handed manipulation, e.g., with the user grasping the handle 17a, 17b of each shaft member 12a, 12b (with a finger disposed through each of finger holes 18a, 18b) and moving handles 17a, 17b laterally apart from one another.

Referring now to FIGS. 3-4, in conjunction with FIG. 1, in procedures where it desired to cut tissue at the completion of tissue treatment (or simply where it is desired to grasp and cut tissue), rather than disengaging ratchet mechanism 30 to return jaw members 110, 120 to the spaced-apart position, ratchet mechanism 30 remains engaged such that jaw members 110, 120 are maintained in the desired approximated position. In this position, trigger 152 may be actuated to cut tissue grasped between jaw members 110, 120. More specifically, since safety mechanism 180 is disposed in the unlocked condition, the user may grasp trigger 152 and translate trigger 152 proximally from distal end 156 of slot 154 to proximal end 158 of slot 154. As trigger 152 is translated proximally, belt 160 is rotated about posts 162, 164 to thereby translate knife 174 distally from the retracted position to the extended position, wherein knife 174 extends through knife channels 115a, 115b defined within jaw members 110, 120 to cut tissue grasped therebetween.

Actuation of trigger 152, e.g., movement of trigger 152 to proximal end 158 of slot 154 to deploy knife 174, also effects movement of proximal extension 168 of trigger 152 to the second position, wherein proximal extension 168 extends along and adjacent to second ratchet component 136 of second shaft member 12b, which is disposed at least partially within slot 13 of first shaft member 12a. With proximal extension 168 of trigger 152 extending along and adjacent to second ratchet component 36, lateral movement of first and second shaft members 12a, 12b relative to one another is inhibited due to the positioning of proximal extension 168 of first shaft member 12a and second ratchet component 136 of second shaft member 12b relative to one another. That is, proximal extension 168 inhibits lateral movement of second ratchet component 136 of second shaft member 12b within slot 13 of first shaft member 12a, thereby inhibiting lateral movement of first and second shaft members 12a, 12b relative to one another and, thus, inhibiting disengagement of ratchet mechanism 30. As such, when knife 174 is disposed in the extended position, return of jaw members 110, 120 to the spaced-apart position is inhibited. Rather, the slight lateral movement of first and second shaft members 12a, 12b apart from one another to disengage ratchet mechanism 30 is only permitted when knife 174 is disposed in the retracted position, e.g., once trigger 152 is released and returned under the bias of spring 166 (or otherwise returned) back to distal end 156 of slot 154, similarly as described above.

Figure 5:
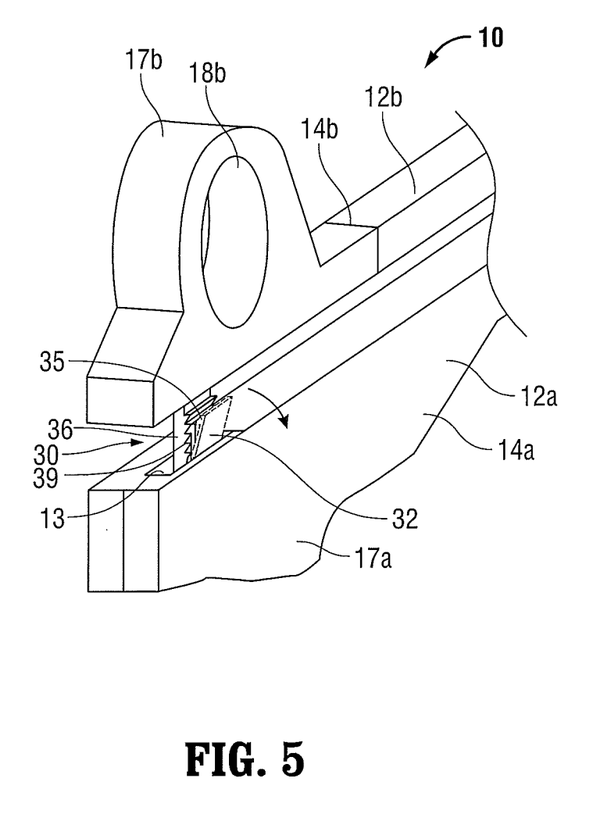
FIG. 5 is an enlarged, rear, perspective view of the proximal end of the forceps of FIG. 1 showing manual disengagement of the ratchet mechanism thereof.

With reference to FIG. 5, in conjunction with FIGS. 1-4, there may be instances where it is necessary to manually override the above-described safety feature to permit jaw members 110, 120 to return to the spaced-apart position even though knife 174 remains disposed in the extended position. In such instances, the engagement between first and second ratchet components 32, 36 of ratchet mechanism 30 may be manually overridden. However, in order to manually override this safety feature, two-handed operation is required, whereby the user manually grasps and flexes the at least partially flexible first ratchet component 32 of first shaft member 12a away from the substantially rigid second ratchet component 36 of second shaft member 12b with one hand, while simultaneously applying a separation force (or retaining the relative position) between first and second shaft members 12a, 12b to disengage ratchet mechanism 30. Requiring a two-handed manual override reduces the likelihood of accidental or inadvertent override, while still providing the ability, where necessary, to manually override the above-described safety feature. For convenience and ease of operation, forceps 10 is otherwise configured for single-handed operation, as can be appreciated in view of the foregoing.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of the embodiments. Those skilled in the art will envision other modifications within the scope and spirit of the claims appended hereto.

What is claimed is:

1. A forceps, comprising:
   an end effector assembly including first and second jaw members movable relative to one another between a spaced-apart position and an approximated position for grasping tissue therebetween;
   at least one handle coupled to the end effector assembly and movable between an open position and a closed position for moving the first and second jaw members between the spaced-apart position and the approximated position;
   a ratchet mechanism including first and second ratchet components, the first and second ratchet components configured to engage one another upon movement of the at least one handle to the closed position to retain the first and second jaw members in the approximated position;
   a knife selectively movable between a retracted position and an extended position, wherein the knife extends between the first and second jaw members to cut tissue therebetween; and
   a safety member biased towards a blocking position inhibiting extension of the knife when the first and second jaw members are disposed in the spaced-apart position, wherein upon movement of the first and second ratchet components into engagement with one another to retain the first and second jaw members in the approximated position, one of the first and second ratchet components urges the safety member to an unblocking position, thereby permitting extension of the knife.

2. The forceps according to claim 1, further comprising a trigger assembly coupled to the knife, the trigger assembly including a trigger movable between a first position and a second position for moving the knife between the retracted position and the extended position.

3. The forceps according to claim 2, wherein the trigger assembly further includes a belt rotatably disposed about first and second posts, the trigger coupled to the belt on one side thereof and the knife coupled to the belt on the other side thereof such that movement of the trigger in a first direction effects rotation of the belt about the first and second posts and movement of the knife in a second, opposite direction.

4. The forceps according to claim 2, wherein the safety member is pivotable between the blocking position, wherein at least a portion of the safety member is disposed in a travel path of the trigger to inhibit movement of the trigger from the first position, and the unblocking position, wherein the at least a portion of the safety member is displaced from the travel path of the trigger to permit movement of the trigger from the first position.

5. The forceps according to claim 2, wherein, in the second position, at least a portion of the trigger is positioned adjacent one of the first and second ratchet components to inhibit disengagement of the first and second ratchet components from one another.

6. The forceps according to claim 1, wherein the at least one handle is movable from the open position to a plurality of closed positions for moving the first and second jaw members between the spaced-apart position and a plurality of approximated positions, and wherein the first and second ratchet components are configured to engage one another at a plurality of incremental positions corresponding to the plurality of approximated positions of the first and second jaw members.

7. A forceps, comprising:
   an end effector assembly including first and second jaw members movable relative to one another between a spaced-apart position and an approximated position for grasping tissue therebetween;
   at least one handle coupled to the end effector assembly and movable between an open position and a closed position for moving the first and second jaw members between the spaced-apart position and the approximated position;
   a ratchet mechanism including first and second ratchet components configured to engage one another upon movement of the at least one handle to the closed position to retain the first and second jaw members in the approximated position;
   a knife selectively movable between a retracted position and an extended position, wherein the knife extends between the first and second jaw members to cut tissue therebetween; and
   a trigger coupled to the knife and movable between a first position and a second position for moving the knife between the retracted position and the extended position, the trigger including an extension member movable therewith and operably positioned such that wherein, in the second position, the extension member is positioned adjacent one of the first and second ratchet components to inhibit disengagement of the first and second ratchet components from one another.

8. The forceps according to claim 7, further comprising a belt rotatably disposed about first and second posts, the trigger coupled to the belt on one side thereof and the knife coupled to the belt on the other side thereof such that movement of the trigger in a first direction effects rotation of the belt about the first and second posts and movement of the knife in a second, opposite direction.

9. The forceps according to claim 7, wherein the at least one handle is movable from the open position to a plurality of closed positions for moving the first and second jaw members between the spaced-apart position and a plurality of approximated positions, and wherein the first and second ratchet components are configured to engage one another at a plurality of incremental positions corresponding to the plurality of approximated positions of the first and second jaw members.

10. The forceps according to claim 7, wherein at least one of the first and second ratchet components is formed at least partially from a flexible material to permit manual override to disengage the first and second ratchet components from one another when the trigger is disposed in the second position.

11. The forceps according to claim 7, further comprising a safety member biased towards a blocking position inhibiting movement of the trigger to the second position when the jaw members are disposed in the spaced-apart position, wherein, upon movement of the first and second ratchet components into engagement with one another to retain the first and second jaw members in the approximated position, one of the first and second ratchet components urges the safety member to an unblocking position, thereby permitting movement of the trigger to the second position.

12. The forceps according to claim 11, wherein the safety member is pivotable between the blocking position, wherein at least a portion of the safety member is disposed in a travel path of the trigger to inhibit movement of the trigger from the first position, and the unblocking position, wherein the at least a portion of the safety member is displaced from the travel path of the trigger to permit movement of the trigger from the first position.

13. A forceps, comprising:
   first and second jaw members movable relative to one another between a spaced-apart position and an approximated position for grasping tissue therebetween;
   first and second ratchet components operably associated with the first and second jaw members, the first and second ratchet components configured to engage one another upon movement of the first and second jaw members to the approximated position to retain the first and second jaw members in the approximated position;
   a knife assembly including a knife selectively movable between a retracted position and an extended position, wherein the knife extends between the first and second jaw members to cut tissue therebetween; and
   a safety member biased towards a blocking position, wherein the safety member interferes with the knife assembly to inhibit movement of the knife from the retracted position,
   wherein upon movement of the first and second ratchet components into engagement with one another to retain the first and second jaw members in the approximated position, one of the first and second ratchet components urges the safety member to an unblocking position wherein the safety member is displaced from the knife assembly permitting extension of the knife, and
   wherein, in the extended position of the knife, a portion of the knife assembly interferes with the first and second ratchet components to inhibit disengagement of the first and second ratchet components.

* * * * *